United States Patent [19]

Norvell

[11] Patent Number: 5,016,622
[45] Date of Patent: May 21, 1991

[54] WATER IMPERMEABLE, WATER VAPOR PERMEABLE ORTHOPEDIC CAST

[76] Inventor: Jean Norvell, 30 Park Dr., Silverbrook, Newark, Del. 19713

[21] Appl. No.: 504,709

[22] Filed: Apr. 4, 1990

Related U.S. Application Data

[63] Continuation of Ser. No. 180,650, Apr. 4, 1988, abandoned, which is a continuation-in-part of Ser. No. 43,201, Apr. 27, 1987, abandoned.

[51] Int. Cl.$^5$ .............................................. A61F 5/04
[52] U.S. Cl. ...................................................... 128/91 R
[58] Field of Search ............... 128/90, 89 R, 91, 91 R, 128/82.1, 155, 156; 427/2; 206/219; 428/252, 315.5, 316.6, 422, 198, 315

[56] References Cited

U.S. PATENT DOCUMENTS

| | | | |
|---|---|---|---|
| 3,785,479 | 1/1974 | Smith | 206/219 |
| 3,826,252 | 7/1974 | Laico | 128/91 R |
| 3,882,857 | 5/1975 | Woodall, Jr. | 128/90 |
| 4,194,041 | 3/1980 | Gore et al. | 428/315 |
| 4,235,228 | 11/1980 | Gaylord, Jr. et al. | 128/91 R |
| 4,238,522 | 12/1980 | Potts | 427/2 |
| 4,273,115 | 6/1981 | Holland et al. | 128/90 |
| 4,387,710 | 6/1983 | Beatty, III | 128/91 R |
| 4,443,511 | 4/1984 | Worden et al. | 428/198 |
| 4,676,234 | 6/1987 | Wegner | 128/90 |

Primary Examiner—Robert A. Hafer
Assistant Examiner—Michael Brown

[57] ABSTRACT

An immobilizing orthopedic cast is provided made of an inner liquid water-impermeable, water vapor-permeable protective sleeve next to the skin, a resilient padding layer, and a plaster or resin/glass fiber outer immobilizing layer. A microporous expanded polytetrafluoroethylene membrane protective sleeve material provides the above properties for a cast which will dry itself inside and the skin it covers, is bacteria proof, and is not a host for bacteria.

2 Claims, 1 Drawing Sheet

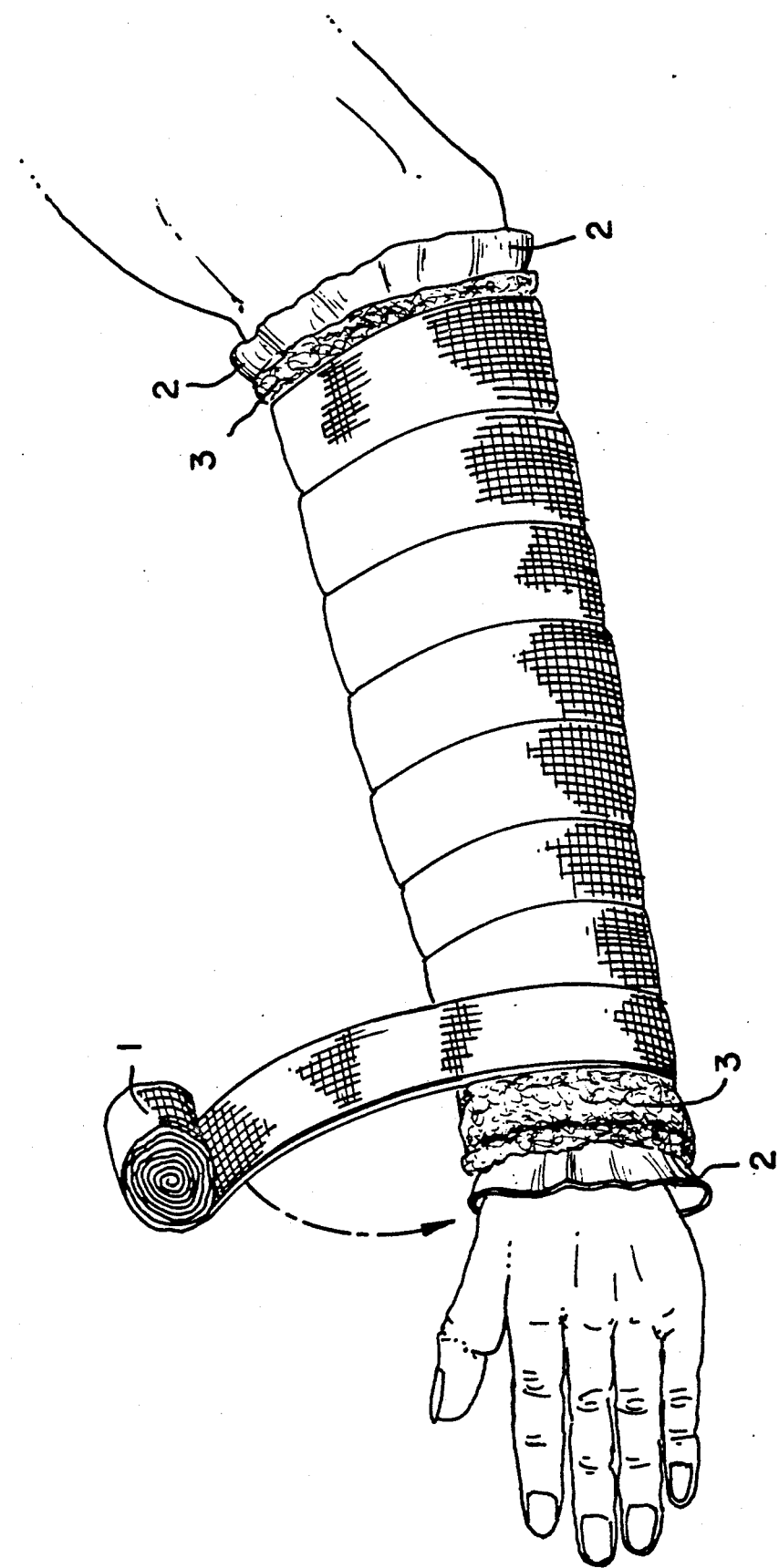
FIG. I.

WATER IMPERMEABLE, WATER VAPOR PERMEABLE ORTHOPEDIC CAST

This application is a continuation of U.S. patent application Ser. No. 07/180,650, filed Apr. 4, 1988, abandoned, which is a continuation-in-part of application U.S. patent application Ser. No. 07/043,201, filed Apr. 27, 1987. now abandoned.

BACKGROUND OF THE INVENTION

The present invention relates to an orthopedic cast which is immobilizing, but allows the skin to function in a normal way. It is characterized by a protective sleeve, adapted to be positioned about a portion of the body of the wearer, that makes the skin under the cast impervious to liquid water and wetness, because it transmits water or perspiration or urine in the form of water vapor away from the skin of the wearer. This provides for increasing comfort and cleanliness of that wearer.

In applying a conventional plaster-of-paris cast, it is standard practice to first cover the body member being treated with a protective cloth bandage or wrap, such as cotton or polyester knit fabric. The protective cloth-covered body member is then covered with cotton or polyester padding to provide a soft resilient padded protective liner. This padding is then overwrapped with wetted plaster-of-paris, in woven cloth wrapping of sufficient length and to such a thickness, so as to provide an immobilizing structure of adequate strength and durability for the intended length of its stay in place on the body member being treated.

It is also known to make casts from glass fiber materials, which consist of heat-softened or curable organic polymeric resins coated on glass fibers which have been woven into fabrics or are formed into unwoven open fibrous mats. Such flexible coated glass fabrics are wrapped while warm about a body member to be immobilized in much the same manner as plaster-containing cloth and allowed to cool and harden after the cast is formed. Woodall, U.S. Pat. No. 3,882,827, describes a resin/glass fiber composite method as do U.S. Pat. Nos. 4,273,115 and 4,238,522.

While the conventional plaster-of-paris casting system and the glass fiber casting system are in widespread use, they have several disadvantages. Both types of cast are considered in the art to be non-breathable and both must be kept dry inside the cast since they cannot breathe.

It is also true that while the casts themselves are impervious to water and not affected by immersion in water, the skin is wet under the cast. A lack of air to dry the skin could permit maceration of the skin under the cast, thus opening it to attack by bacteria.

An additional problem with many casts is that odor develops owing to retention of perspiration and body oils in the cast. As the body secretions or wound drainage are absorbed into the cast padding and ultimately into the cast itself, it may generate a very foul odor. This may become so objectionable as to require a complete change of cast. Deodorants are available for incorporation into the cast material or padding at the time of application, but these have generally proven to be ineffective and most are no longer in use.

Skin erosion and subsequently formed pustules that eminate from blocked hair follicles may cause extreme itching and discomfort for a patient wearing a conventional cast. Additionally, urine soaked casts, particularly in the case of Spica casts worn by infants for several months at a time, have wet padding in constant touch with the skin and therefore unable to dry, resulting often in ulcerated areas on the skin.

BRIEF DESCRIPTION OF THE DRAWINGS

FIG. 1 shows a human arm with a protective sleeve of this invention drawn over it. A roll of plaster or plastic resin/glass fiber wrap is being wound around the arm and sleeve.

DESCRIPTION OF PREFERRED EMBODIMENTS

The present invention is an immobilizing orthopedic cast which is characterized by impermeability to liquid water, which also includes perspiration, urine, or any other largely aqueous-based solution or mixture which is ordinarily encountered in daily life by a person wearing an immobilizing cast.

The cast of this invention is comprised of an inner protective, preferably heat sealed, sleeve of approximately cylindrical configuration to be worn against the skin, followed by a layer of soft, resilient cotton or polyester padding wound, folded, or otherwise formed into a protective layer about the protective sleeve, and formed about both of these layers an immobilizing plaster-of-paris or organic polymer resin/glass fiber composite splinting material.

This preferred form of protective wrapper is a heat-sealed sleeve of a porous liquid water impenetrable, water vapor permeable organic polymeric membrane, preferably of porous expanded polytetrafluoroethylene. This is characterized by properties which permit water, perspiration, or urine to vaporize away from the skin through the membrane by moisture vapor transmission so that the skin remains dry. Moisture vapor transmission of the membrane is the operative mechanism here, not air permeability. The wrapper of the invention is made from a composite membrane which has a continuous hydrophilic layer that transports water by an absorption-evaporation mechanism. The hydrophilic layer is attached to a microporous hydrophobic polymer layer which permits no detectable passage of liquid water to 100 pounds per square inch (psi). Any known membrane having the requisite properties may be used for this layer of the cast of this invention, although the preferred materials are the microporous expanded polytetrafluoroethylene membranes described in U.S. Pat. Nos. 4,194,041 and 4,443,511. Also utilizable are microporous polypropylene films and polyurethane films and tightly woven fabrics of polyolefin fibers and polytetrafluoroethylene and other fluorinated polymer fibers.

Breathability is achieved by evaporation of water inside the inner surface of the membrane, followed by gaseous diffusion of water vapor through the membrane to the outside. This ensures that the surface of the skin remains dry, thus guarding against immersion skin and skin irritation. Because of the intrinsic pore size of the membrane (9 billion per square inch), the membrane also serves to deter bacterial development, since it is a natural barrier to bacteria which cannot pass through pores of such small size. Also, the membrane has no nutritive substance for bacteria to feed upon. Thus, odor caused by rampant bacterial growth on moist skin unable to dry will not occur. Body secretions or wound drainage cannot seep into padding or ultimately into the cast itself. Therefore, odor is greatly reduced.

A heat-sealed tube 2 of the membrane is placed over the area to be immobilized and overwrapped, such as the arm shown in FIG. 1. The membrane tube 2 is then covered or wrapped with a layer of, for instance, soft cotton or polyester padding 3, leaving small ends of membrane 2 uncovered. These may later be trimmed off after the cast has been completely formed and cured or may be folded up over a first layer of the wetted cloth plaster-of-paris web composite wrapping 1 which is now wrapped around the padded, membrane-covered area to be immobilized and anchored or buried inside layers of the wrapping. The cast is completed when an immobilizing thickness of material has been added and it has hardened sufficiently. Such liquid water that might enter the plaster layer of the cast during wear cannot of course penetrate the protective membrane sleeve 2 to harm the wearer and will evaporate through the padding or the outer surface of the cast. Most plaster casts are also air impermeable as well.

Alternatively to the water-wet cloth/plaster-of-paris immobilizing layer, an organic polymer resin-impregnated or coated glass fiber cloth, roving. non-woven mesh, mat, or other glass or plastic fiber material in appropriately sized strips may be wound around the padding layer and the protective sleeve to form an immobilizing orthopedic cast. Many of these materials are warmed to levels above room temperature but to heat levels well tolerable by the body, and while soft, are wound, formed or shaped into a cast which then hardens fairly rapidly to an immobilizing stiffness. These resin/glass fiber casts are usually waterproof in practice, transmit little water vapor, and are not air breathable.

Alternatively to a heat-sealed tube of membrane an overlapped wrap of the same or similar membrane material shown above may be used. Enough of the membrane must be used to overlap about itself on the area to be immobilized by a plaster or polymer/fiber cast so as to achieve good contact between the layers of member to insure waterproofness of the membrane protective warp. This way of using membrane requires more membrane to cover a given area than a heat-sealed tube of the same membrane on the same area and is consequently expensive, but is functional in this invention and may be useful for covering irregular or non-tubular type areas or used under emergency or other circumstances where no heat-sealed tube is available. Membrane formed into a tube by sealing pieces of it together with adhesives which will adhere sufficiently to polytetrafluoroethylene or other polymer membranes useful in this invention can also be used in place of the preferred heat-sealed membrane. Such adhesives may include epoxy, polyurethane, or thermoplastic fluoropolymers.

It will be apparent to those skilled in the art that various modifications and variations could be made in materials and methods for making the casts without departing from the scope or spirit of the invention and the scope of the invention is delineated only by the appended claims.

I claim:

1. An immobilizing orthopedic cast, comprising:
    (a) an inner protective sleeve adjacent the skin, said sleeve consisting essentially of a composite membrane comprising a liquid water impermeable water vapor permeable polymeric membrane layer and a hydrophilic layer attached to the polymeric layer;
    (b) a layer of resilient padding positioned around said inner protective sleeve; and
    (c) an outer immobilizing layer positioned around said layer of resilient padding.

2. The immobilizing orthopedic cost of claim 1 wherein the polymeric layer is expanded polytetrafluoroethylene.

* * * * *